Oct. 18 1949. H. C. SWIM Plant Pat. 883
ROSE PLANT
Filed March 23, 1948
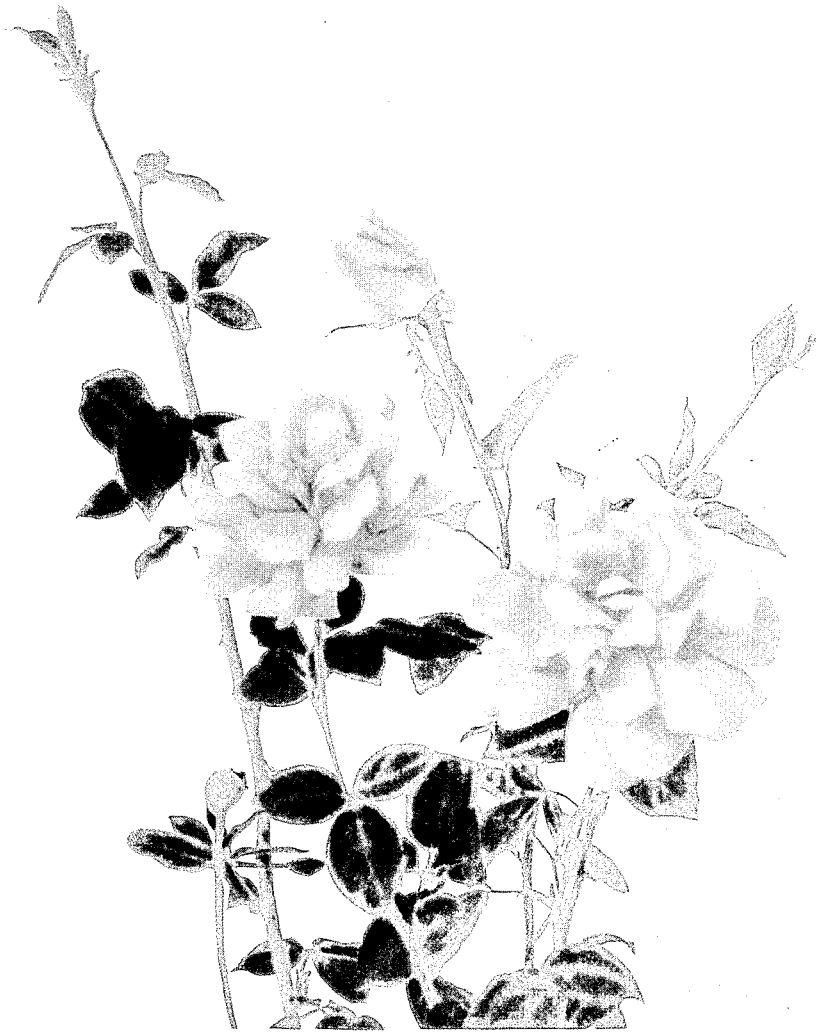
Inventor
H. C. Swim
By Robb & Robb
Attorneys Patented Oct. 18, 1949

Plant Pat. 883

UNITED STATES PATENT OFFICE

883

ROSE PLANT

Herbert C. Swim, Ontario, Calif., assignor, by mesne assignments, to Eldon Pinkeney Dering, doing business as Peterson & Dering, Scappoose, Oreg.

Application March 23, 1948, Serial No. 16,590

1 Claim. (Cl. 47—61)

The present invention relates to a new and distinct variety of hybrid tea rose plant, and particularly to one adapted for cut flowers and garden display.

It may be noted that an object in view in crossing the varieties here used was twofold; first to obtain a long form of bud, so important in the field of cut flowers, and second, to obtain a large showy flower which is a feature of special utility in garden decoration.

More specifically, this new variety of rose possesses the following combination of characteristics:

(1) A vigorous, tall-growing plant of the bush-rose type easily growing to five feet and occasionally to as much as seven feet.

(2) A very long flower stem relatively free of thorns and clothed by a normal amount of medium-heavy glossy foliage of large size.

(3) Flower buds of relatively great length at the stage appropriate for cutting equalling or exceeding the length of the buds of any other variety known to me.

(4) A color in bud and flower substantially as described herein that is distinct from the color of any other variety known to me in commerce.

This new variety is distinct from its seed parent, "Contrast," in the following characters:

(1) In the bud stage it has much greater length than "Contrast" and in the flower stage it is characterized by more informality and with a tendency to develop a somewhat higher center than is found in "Contrast." It does not have the tendency to a cabbage center as found in "Contrast."

(2) A substantially different color both in bud and in open flower. As is indicated by the name, the variety "Contrast" attains deep contrast between the inner and outer surfaces of the petal. This is apparent in both bud and open flower. This deep contrast in color between the two surfaces of the petals is not a characteristic of this new variety.

This new variety differs from its pollen parent, "Charlotte Armstrong," as follows:

(1) It has glossy foliage whereas the foliage of "Charlotte Armstrong" is non-glossy.

(2) A more slender habit of growth than is typical of the plant of "Charlotte Armstrong" which is usually described as upright-spreading.

(3) The relatively thornless nature of the stems as contrasted with those of "Charlotte Armstrong" which are described as having numerous large and small thorns.

(4) Bud and flower color characterized by giving a general appearance of being more orange than is characteristic of the buds and flowers of "Charlotte Armstrong."

Asexual reproduction shows that these characteristics hold true through succeeding propagations.

In the accompanying drawings are illustrated specimens of this new rose, showing the flowers at different stages of development and the substantial absence of thorns.

The following is a detailed description of the new variety, all references to color being in accordance with the R. F. Wilson's Horticultural Colour Chart, except where indicated to be in accordance with Ridgeway's Color Standards and Nomenclature:

Type: Tall; bush; outdoor; seedling; for cut flowers and garden decoration.

Class: Hybrid tea.

Breeding: Seedling.

*Seed parent.*—"Contrast" (unpatented).

*Pollen parent.*—"Charlotte Armstrong" (Plant Patent No. 455).

Propagation: Holds its distinguishing characteristics through succeeding propagations by budding.

*Flower*

Locality where grown: Ontario, California.

Flowers borne: Usually singly, occasionally two or three or more to stem in irregular cluster; on strong, long stems.

Quantity of bloom: Free; outdoors.

Continuity: Continuous during growing season.

Fragrance: Moderate; spicy.

Bud:

*Peduncle.*—Long; medium to heavy in caliper; erect; almost smooth; few gland-tipped cilia and hairs. *Color.* — deep Chrysolite Green, Plate XXXI (Ridgway).

*Before calyx breaks.*—*Size*—medium to large. *Form*—long; pointed, with a conspicuous neck; with foliaceous appendages and glandular bloom on the surface of the bud; with slender, much cut foliaceous parts extending beyond the tip of the bud equal to ¾ or more of its length.

*As calyx breaks.*—*Color*—near Carmine Rose, Plate 621, page 75. *Sepals*—inner surface with fine, woolly tomentum. When the margin is not covered by an adjacent sepal, it has woolly tomentum and stipitate glands on margin; but when margin is covered by adjacent sepal, margin has only woolly tomentum.

*As first petal opens.*—*Size*—medium to large. *Form*—very long, pointed; usually from 1¾" to 2½". *Color* — outside — large blotch of Aureolin, Plate 3/1, page 3, at base of petal, shading from Porcelain Rose, Plate 620/1, page 147, to Porcelain Rose, Plate 620, page 147 at outer margin. Inside—blotch of Lemon Yellow, Plate 4, page 4, at base of petal, shading through Geranium Lake, Plate 20/1, page 20, to near Carmine, Plate 21, page 21

*Opening.*—Opens up well.

Bloom: Size, when fully open—medium to large; 4″ to 5″.

*Petalage.*—Semi-double to double (more petals, but the stamens not hidden); from 18 to 22 petals; arranged regularly. Usually with 3 to 6 petaloids at center.

*Form.*—High centered at first; becoming flat; petals remaining at first very loosely rolled outward; becoming later, at maturity, tightly rolled outward.

Petals: Thick; leathery; with inside velvety and outside satiny.

*Shape.*—Outside—obovate; scalloped with apex with one notch. Intermediate—obovate; scalloped with apex occasionally with one notch. Inside—obovate; scalloped irregular with apex with one or two notches.

*Color.*—Colors may be modified by being margined, blotched, shaded or washed with other colors.

This description of a newly opened flower was made from a rose grown outdoors in the month of September, at Ontario, California:

*Color.*—*Outside petal*—outside surface: base, Aureolin, Plate 3/2, page 3, shading toward apex to Carmine Rose, Plate 621/1, page 75, with blotches of Carmine Rose, Plate 621/2, page 75; inside surface: base, Aureolin, Plate 3/1, page 3, shading toward apex to near Geranium Lake, Plate 20/1, page 20, becoming blotched and shaded near center and outer margins with Rose Madder, Plate 23/2, page 23. *Intermediate petal*—outside surface: base, Aureolin, Plate 3/2, page 3, shading toward apex to Carmine Rose, Plate 621/1, page 75; inside surface: base, Aureolin, Plate 3/1, page 3, shading toward apex to near Crimson, Plate 22/1, page 22, with a narrow outer margin of Crimson, Plate 22/3, page 22. *Inner petal*—outside surface: base, Aureolin, Plate 3/2, page 3, shading toward apex to Carmine Rose, Plate 621, page 75; inside surface: base, Aureolin, Plate 3/1, page 3, shading toward apex to near Crimson, Plate 22/1, page 22, becoming near outer margin Crimson, Plate 22/2, page 22, with a narrow outer margin of Crimson, Plate 22/3, page 22.

This description was made from a rose that was open for three days indoors in the month of September, at Ontario, California:

*Color.*—Outside petal—outside surface: base, Aureolin, Plate 3/2, page 3, shading toward apex to Rose Bengal, Plate 25/3, page 25, blotched and shaded with Rose Bengal, Plate 25/2, page 25; inside surface: base, Aureolin, Plate 3/1, page 3, shading toward apex to near Rose Bengal, Plate 25/1, page 25, washed with near Rose Bengal, Plate 25, page 25. *Inside petal*—outside surface: base, Aureolin, Plate 3/2, page 3, shading toward apex to Rose Bengal, Plate 25/3, page 25, blotched and shaded with Rose Bengal, Plate 25/2, page 25; inside surface: base, Aureolin, Plate 3/1, page 3, shading toward apex to near Rose Bengal, Plate 25/1, page 25, washed with near Rose Bengal, Plate 25, page 25.

*General color effect.*—Newly opened flower—near Crimson, Plate 22/1, page 22. Three days open—near Rose Bengal, Plate 25/1, page 25.

*Behavior.*—Drop off cleanly; fading slightly purple; affected by hot and dry weather by becoming lighter in color.

*Flower longevity.*—On bush in garden—three to four days in September. Cut roses grown outdoors kept at living room temperatures—three days in September.

*Reproductive organs*

Stamens: Medium in number, usually about 50; arranged regularly about pistils.

Filaments: Medium to long; 7 mm. to 12 mm.; most with anthers. *Color*—near Lemon Yellow, Plate 4, page 4, at base shading to Lemon Yellow, Plate 4/2, page 4, near apex.

Anthers: Medium in size; all open at once. *Color*—Indian Yellow, Plate 6/2, page 6, shading to Yellow Ochre, Plate 07/2, page 101, at outer margins.

Pollen: Moderate. *Color*—near Yellow Ochre, Plate 07/1, page 101.

Pistils: Medium in number, usually about 30 to 35.

Styles: Uneven; medium in length from 6 to 10 mm. long; thin; loosely bunched. *Color*—near Current Red, Plate 821, page 167, near stigma, shading lighter toward base.

Stigma: Gray-white, almost translucent becoming pinkish color at edge.

Ovaries: Some protruding from calyx.

Hips: Globular; smooth; walls thick, fleshy. *Color*—near Absinthe Green, Plate XXXI (Ridgway), later becoming near Olive-Ocher. Plate XXX (Ridgway).

Sepals: Falling soon; moderately long; curled, recurved. *Color*—on maturing hips—inside: near Sepia, Plate XXIX (Ridgway); outside—near Snuff Brown, Plate XXIX (Ridgway).

Seeds: Few to many; from 4 to 10 seeds; medium to large.

*Plant*

Foliage:

*Leaves.*—Compound of usually five leaflets; large; medium heavy; glossy; normal in quantity.

*Leaflets.* — Shape—Ovate lanceolate with apex acute; base round; margin doubly serrate.

*Color.*—

*Mature*—upper surface—near Dark Dull Yellow-Green, Plate XXXII (Ridgway); under surface—near Asphodel Green, Plate XLI (Ridgway). *Young*—upper surface—near Light Cress Green, Plate XXXI (Ridgway) washed with near Perilla Purple, Plate XXXVII (Ridgway); under surface—near Absinthe Green, Plate XXXI (Ridgway) washed with Vandyke Red, Plate XIII (Ridgway).

*Rachis.*—Medium in caliper. Upper side—grooved, hairy and glandular. Under side—sparsely hairy and prickly with stipitate glands.

*Stipules.* — Moderately short; moderately narrow; with moderately short points turning out at an angle of less than 45°.

*Disease.*—Resistant to mildew.

Growth:

*Habit.*—Bushy; tall; upright; moderately branched.

*Growth.*—Very vigorous.

*Canes.*—Medium to heavy in caliper.

*Main stems.*—*Color*—Rainette Green, Plate XXXI (Ridgway), with stripes of callus of near Verona Brown, Plate XXIX (Ridgway). *Large prickles*—Very few; medium to long; hooked straightly downward; with long narrow base. *Color*—near Vandyke Brown, Plate XXVIII (Ridgway). *Small prickles and hairs*—none.

*Branches.*—*Color*—Rainette Green, Plate XXXI (Ridgway). *Large prickles*—very few; medium length; hooked straightly downward; with short narrow base. *Color*—Cinnamon-Brown, Plate XV (Ridgway). *Small prickles and hairs*—none.

*New shoots.*—*Color*—Absinthe Green, Plate XXXI (Ridgway), often washed with Deep Hellebore Red, Plate XXXVIII (Ridgway). *Large prickles*—very few; medium length; hooked straightly downward; with short narrow base. *Color*—near Etruscan Red, Plate XXVII (Ridgway). *Small prickles and hairs*—none.

I claim:

A new and distinct variety of hybrid tea rose plant, characterized as to novelty by its vigorous habit of growth to from five to seven feet; production of long flower stems relatively free of thorns, and glossy foliage of large size; flower buds of relatively great length appropriate for cut flower utility, and a color in bud and flower distinct from any other known variety, substantially as shown and described.

HERBERT C. SWIM.

No references cited.